United States Patent [19]

Tanaka et al.

[11] Patent Number: 4,643,196

[45] Date of Patent: Feb. 17, 1987

[54] BIOPSY NEEDLE SET

[75] Inventors: Masataka Tanaka, Nagano; Masao Ohto, Togane; Tetsuo Sekine, Tokyo; Koji Isobe; Masaru Maruyama, both of Nagano, all of Japan

[73] Assignee: Hakko Electric Machine Works Co., Ltd., Japan

[21] Appl. No.: 726,069

[22] Filed: Apr. 23, 1985

[30] Foreign Application Priority Data

Oct. 24, 1984 [JP]  Japan .......................... 59-160900[U]
Nov. 26, 1984 [JP]  Japan .......................... 59-178791[U]

[51] Int. Cl.⁴ .................................................. A61B 10/00
[52] U.S. Cl. ................................................... 128/753
[58] Field of Search ................................. 128/751–754

[56] References Cited

U.S. PATENT DOCUMENTS

| | | | |
|---|---|---|---|
| 3,606,878 | 9/1971 | Kellogg, Jr. ..................... | 128/753 |
| 3,882,849 | 5/1975 | Jamshioi .......................... | 128/753 |
| 4,308,875 | 1/1982 | Young ............................... | 128/753 |
| 4,396,021 | 8/1983 | Baumgartner .................... | 128/751 |
| 4,513,754 | 4/1985 | Lee .................................... | 128/754 |
| 4,532,935 | 8/1985 | Wang ................................ | 128/754 |

Primary Examiner—William E. Kamm
Attorney, Agent, or Firm—Aaron B. Karas

[57] ABSTRACT

In application of a biopsy needle set which is utilized for collecting diseased tissue sections from internal organs in a human body without requiring surgical operation, it is desirable to be certainly taken out the tissue sections by single puncture and to decrease injury of such diseased part in addition, to reduce pain in the patient at the time of sticking into the human body with the needle. In an end of suction type biopsy needle set containing double needle set of an outer needle and an inner needle, the outer needle is narrowed to form a closely contacting portion with the inner needle, whereby negative pressure can be accumulated in a cylinder at the early stage of such suction, while thus accumulated negative pressure is transferred to an opening of the outer needle at the moment when the withdrawn inner needle is passed through the above described closely contacting portion, so that such suction force sufficient for collecting the tissue sections is produced. In this case, valve function of the needle tip construction in the above biopsy needle set can realize reliability of collecting the tissue sections. Furthermore suction can be in one-handed operation by such construction that a plunger is provided with a knob projecting through the notched split formed on the cylinder.

8 Claims, 11 Drawing Figures

BIOPSY NEEDLE SET

BACKGROUND OF THE INVENTION

1. Field of the Invention

The present invention relates to a biopsy needle set for sucking and collecting tissue sections in diseased parts such as internal organs and the like of a patient for obtaining test specimen, and particularly to a biopsy needle set which can suck certainly tissue sections and maintain stably the suction force during removal of such needle from the human body.

2. Description of the Prior Art

As a conventional biopsy needle set, there has been proposed, for example, a collecting instrument of internal organ tissue sections, as shown in Japanese Patent Publication No. 52575/1981, which comprises, as illustrated in FIGS. 1 through 4, a metallic outer needle 1 an end of which is formed into an edge of blade and which is provided with a needle base 2 at the opposite end thereof, a syringe barrel 3 to an end of which the needle base 2 is detachably attached, an inner needle 4 an end of which is formed into a sharp tip portion 4a, a slidably contacting portion 4b having a diameter a little less than a inner diameter of the outer needle 1 extending from said sharp tip portion 4a, and a flat supporting portion 4c extending further from said slidably contacting portion 4b, and a syringe plunger 6 on an end of which mounts a slide packing 5 fitted closely in the inside wall of the syringe barrel 3 to slidably move therein, the inner needle 4 being provided on the end of said syringe plunger 6.

In the above construction, a human body is punctured with the biopsy needle set under such condition where the sharp tip portion 4a of the inner needle 4 is projected from the outer needle 1 and when the sharp tip portion 4a reaches an internal organ, the syringe plunger 6 and the inner needle 4 are relatively retracted from the syringe barrel 3 and the outer needle 1, so that negative pressure is produced in the syringe barrel 3 by withdrawal of the slide packing 5 fitted closely in the syringe barrel 3. Thus, such negative pressure is transmitted to the end of the outer needle 1 through a gap defined between the outer needle 1 and the inner needle 4 and when the syringe barrel 3 is advanced while maintaining the condition as mentioned above, the blade edge of the outer needle 1 cuts off the tissue in a columnar shape. Then, a part of the internal organ which has been in contact with the end of the outer needle 1 is sucked to be led into the outer needle 1. In this state, when the retraction of the syringe plunger 6 is stopped and the outer needle 1 is withdrawn from the body, the tissue sections being in the outer needle 1 as a result of the suction are torn off so that such tissue sections can be taken out from the body.

According to the above conventional example, the slidably contacting portion 4b is formed at the end portion of the inner needle 4, and the gap is defined between the supporting portion 4c extending from the slidably contacting portion 4b and the inside wall of the outer needle 1, such that the supporting portion 4c is not in close contact with the inside wall of the outer needle 1, whereby negative pressure produced in the syringe barrel 3 can be efficiently transmitted to the end of the outer needle 1. Hence, when an internal organ to be colleted is merely punctured slightly with the end of the outer needle 1, a test specimen can be collected so that pain in a patient can be abated. In case of collecting tissue sections, a thick needle having a diameter of 1.05 mm (19 G) or more has been used as the outer needle 1 of a conventional biopsy needle.

In accordance with such conventional collecting instrument of internal organ tissue sections, however, negative pressure transmitted to the end of the outer needle 1 keeps leaking at the slidably contacting portion 4b in case of suction by the syringe plunger 6, so that if it is intended to produce intensive suction force at the end of the outer needle 1, the syringe plunger 6 must be rapidly pulled. Thus there have been such disadvantages that the collection of test specimens becomes unreliable, and that in the case where outer needle 1 is made more slender for abating pain in a patient, only a tissue liquid except tissue sections may be collected because of the weak suction force.

SUMMARY OF THE INVENTION

It is the first object of the present invention to provide a biopsy needle set by which the tissue sections in a diseased part can certainly be collected with more intensive and continuous suction force.

The second object of the present invention is to provide a biopsy needle set in which intensive suction force can be produced even in the case where a needle having a thin diameter is utilized for abating more pain in a patient.

· The third object of the present invention is to provide a biopsy needle set by which suction can be performed in one-handed operation.

The forth object of the present invention is to provide a biopsy needle set by which tissue sections can certainly be collected even from the tissue containing much tissue liquid.

The fifth object of the present invention is to provide a biopsy needle set wherein the rigidity thereof is not decreased even if a slender needle is used for easily puncturing a human body.

According to the present invention, there is proposed a biopsy needle set provided with puncturing needle of a double construction composed of an outer needle secured to an end of a cylinder and an inner needle secured to an end of a plunger, and said outer needle containing slidably said inner needle, comprising said outer needle having the first section where the inside wall of said outer needle is closely in contact with said inner needle at the end portion of said outer needle, and the second section which is not in close contact with said inner needle.

BRIEF DESCRIPTION OF THE DRAWINGS

FIGS. 1 to 4 illustrate an embodiment of publicly known biopsy needle set wherein FIG. 1 is a front view showing an outer needle mounted on a syringe barrel;

FIG. 2 is a front view showing an inner needle secured to the end of a syringe plunger;

FIGS. 3 and 4 are partly enlarged sectional views each showing a state where the inner needle is inserted into the outer needle;

DETAILED DESCRIPTION OF THE INVENTION

Figure 1:
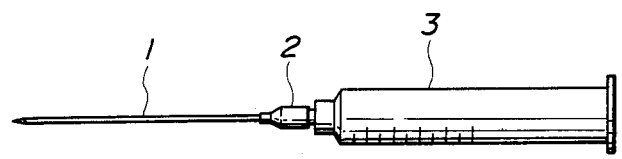
Figure 2:
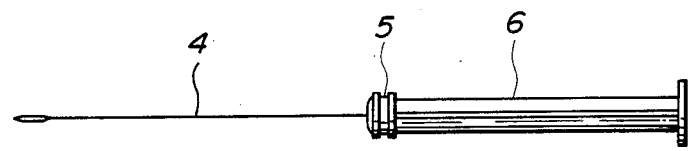
Figure 3:
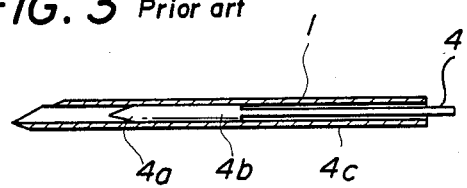
Figure 4:
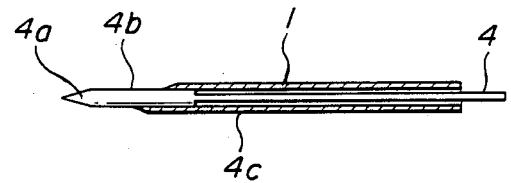

The biopsy needle set according to the present invention will be described in detail hereinbelow by referring to the accompanying drawings.

FIG. 5 through 8 illustrate the first embodiment of the present invention wherein the biopsy needle set comprises the metallic outer needle 21 which is composed of a close contact section A a tip portion of which is formed as a shape of blade, and the inner wall cross section of which may be tapered, a narrowed space section B at the central part thereof, and a reinforced section C the diameter of which is the largest and to the base portion of which a needle base 22 is fixed; the sharp inner needle 28 which has a diameter to be in close contact with the outer needle 21 and a tip portion of which has been obliquely cut down; the cylinder 23 containing a pair of notched splits 24 (provided with a retainer 24a for tentatively holding a plunger knob 31) being symmetrical with respect to the central axis thereof, and the rear end portion of which is covered by cylinder end cap 35 and to the front end portion of which the needle base 22 is detachably attached; and the plunger 30 on the front end portion of which a slide packing 29 is mounted, the inner needle 28 being fixed to an end of the slide packing at the center thereof, and the rear end portion of which is provided with the knob 31.

Figure 7:
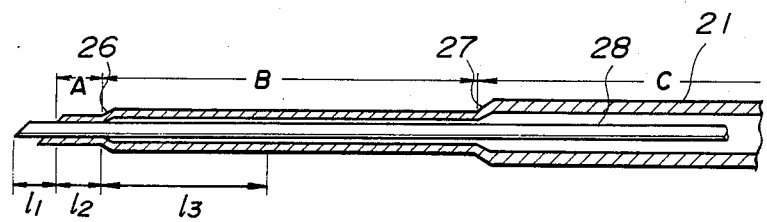
FIG. 7 is an enlarged sectional view showing a part of the outer needle in FIG. 5.
Figure 8:
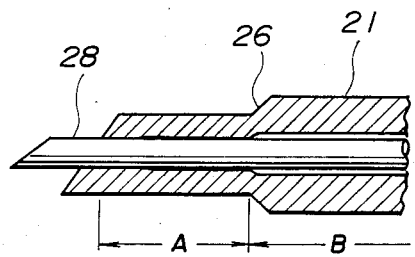
FIG. 8 is an enlarged sectional view showing the end portion of the outer needle in FIG. 5.

In the case where the inner needle 28 is inserted into the outer needle 21 as shown in FIG. 7, air does not substantially flow in the section A since the outer needle is close contact with the inner needle (0.5 mm diameter). In the section B resistance in air flow appears at a certain degree in the case where air flows through an area where the outer needle is in slidable contact with the inner needle (outer and inner diameters of the outer needle being 0.8 mm (21 G) and 0.58 mm, respectively). In the section C, since the gap defined between the outer and inner needles is sufficient, resistance in air flow can be substantially neglected in the case where air flows therethrough (outer and inner diameters of the outer needle being 1.05 mm (19 G) and 0.83 mm, respectively).

Figure 6:
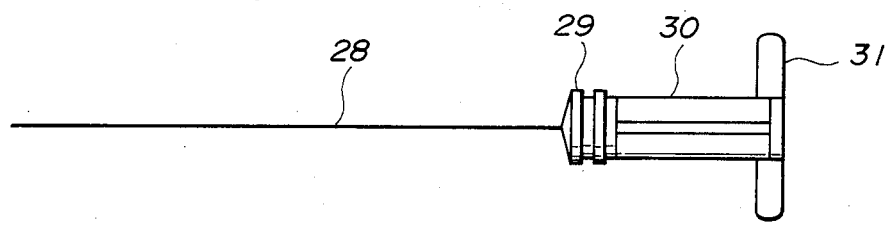
FIG. 6 is a partial view showing the plunger of FIG. 5 which has been rotated at an angle of 90° with respect to the longitudinal axis.

In the case when the plunger 30 provided with the knob 31 as shown in FIG. 6 is contained in the cylinder 23, the aforesaid knob 31 is slidable along the notched split 24 in the body part of the cylinder 23, and the knob 31 is tentatively held in the holding portion 24a defined at the end portion of the notched split 24.

In the above construction, operations and functions of the biopsy needle set in the case when tissue sections are taken out by the use of the present biopsy needle set from internal organs in a human body will be described hereinbelow.

Figure 5:
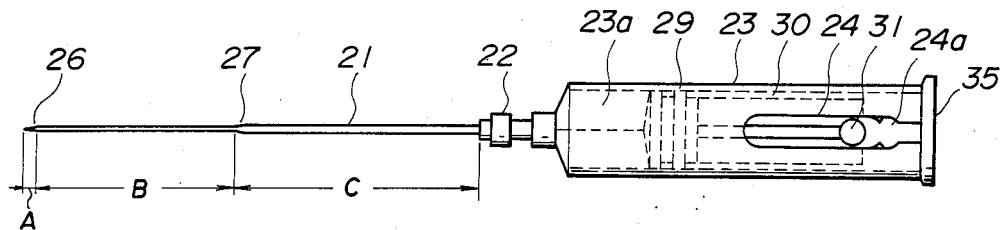
FIG. 5 is a constructional view showing the first embodiment of the biopsy needle set according to the present invention.

First of all, the plunger 30 is pushed to the inside end of the cylinder 23 by moving the knob 31 to the front end portion of the notched split 24 and as a result, such a situation where the tip of the inner needle 28 is projected from the end of the outer needle 21 with a length of about 2 mm is observed. The human body is punctured with the biopsy needle set while maintaining the above projected inner needle 28. When the needle tip reaches the target organ, both projections of the knob 31 are caught by second and third fingers of either hand of an operator, and the plunger 30 is rapidly retracted by pulling the knob 31 until movement of the knob 31 stops due to abutment of the knob 31 against the holding portion 24a while holding the lid 35 by the first finger of the same hand. As a result of the retracting operation of the plunger 30, it slides along the inside wall of the cylinder 23 being in close contact therewith so that negative pressure produces in a space 23a defined by the cylinder 23 and the slide packing 29 disposed at the end of the plunger 30 as shown in FIG. 5. Such negative pressure transmits to the needle tip through the interior of the outer needle 21, so that suction force is produced at the tip of the outer needle 21 because there is a pressure difference between the negative pressure and atmospheric pressure.

Then, when the cylinder 23 is advanced towards the internal organ at the same time of the production of suction force as described above, tissue sections of the internal organ penetrate into the interior space of the outer needle 21 formed by retraction of the inner needle 28, and in addition the tissue sections are sucked because of the aforesaid suction force. After the suction, when the outer needle 21 is drawn from the body, the tissue sections which have been sucked in the outer needle 21 are torn off so that such tissue sections can be taken out from the body.

Figure 9:
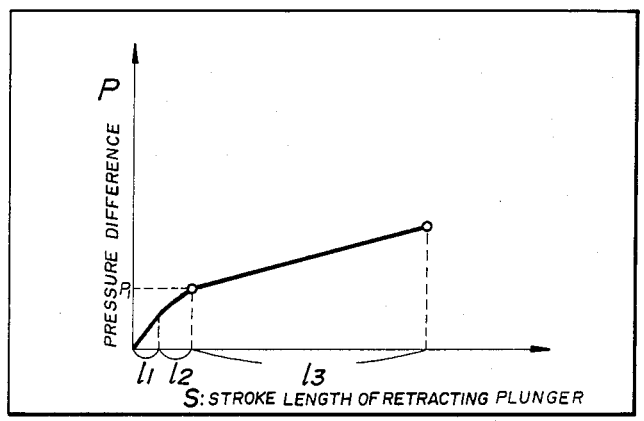
FIG. 9 is a graphical representation illustrating a relationship between stroke length of the retracting plunger and pressure difference produced between the cylinder and the needle tip in an embodiment of the present invention.

A relationship between negative pressure (represented by pressure difference P from atmospheric pressure, and hereinafter referred to simply as "P") produced in the space 23a in the cylinder 23 during the above-mentioned sucking operation and stroke length (hereinafter referred to simply as "S") of the retracting plunger 30 with respect to the cylinder 23 is illustrated in FIG. 9 and the explanation therefor will be made hereinbelow.

The outer needle 21 is provided with the above-mentioned three sections in accordance with changes in the inner diameter thereof. In the case where the inner needle 28 which is in the outermost projected position from the outer needle 21 is rearwardly moved to pass through the section A, S to be required therefor is the sum of a length ($l_1$) of such part of the inner needle 28 which has been projected from the outer needle 21 and the length ($l_2$) of the section A. Since the outer needle 21 is in close contact with the inner needle 28 in this ($l_1+l_2$) stroke, P is sharply increased while pressure difference $P_1$ thus increased is stored. Negative pressure is transmitted to the tip of the outer needle 21 at such moment that the tip of the inner needle 28 passes through the end of narrow portion 26. For this reason, intensive suction force can be produced at the early stage of sucking operation. The inner needle 28 is further retracted to enter the section B, until the plunger abuts upon the holding portion 24a (stroke ($l_3$)) so that it is held tentatively. Even in this ($l_3$) stroke, P increases gradually because the close contact in section A functions as valve means, and such increased P (Negative pressure) is transmitted to the needle tip so that the suction force is produced increasingly during the sucking operation of the stroke ($l_3$). In accordance with the suction force as described above, tissue sections are certainly sucked during whole stage, because suction force is maintained for the reason why negative pressure is increasing gradually above pressure difference $P_1$.

In addition, according to the present embodiment, the plunger 30 is provided with the knob 31 so that suction can be made in one-handed operation. Thus, biopsy can easily be performed while shifting a probe of an ultrasonograph by another hand of the operater to observe a human body to be diagnosed.

According to the construction of the biopsy needle set of the present embodiment, since diameter of the outer needle 21 in said section B is slender, i.e., 21 G (0.8 mm), pain in a patient at the time of puncturing the body with the needle can be reduced, whilst rigidity of the whole outer needle 21 can be elevated because of diameter of the outer needle 21 of 19 G (1.05 mm) in said section C, and in addition negative pressure in the cylinder 23 can easily be transmitted to said section B since inner diameter of the outer needle 21 is 0.83 mm in said section C.

Figure 10:
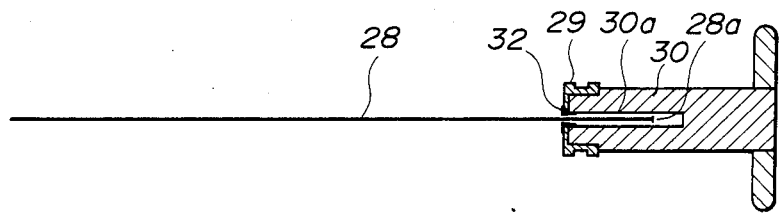
FIG. 10 is a partial sectional view showing an inner needle and a plunger in the second embodiment of the present invention.

The biopsy needle set according to the second embodiment of the present invention is constructed, as shown in FIG. 10, unlike the first embodiment in such that the plunger 30 comprises a longitudinal slot 30a of a desired length defined therein while a stopper 28a is formed on the rear end of the inner needle 28 which is slidable in the longitudinal slot 30a. Further there is provided another stopper 32 for anchoring the stopper 28a of the inner needle 28 in the case when the plunger is moved for suction of tissue sections as well as retraction of the needle. In this embodiment, when the stopper 28a of the inner needle 28 abuts upon the bottom of the longitudinal slot 30a, the tip of the inner needle 28 becomes projected about 2 mm beyond the tip of the outer needle 21 as shown in FIG. 7.

In accordance with the above construction, even if the plunger 30 is drawn back, the inner needle 28 does not retract during the stroke of the plunger 30 corresponding to the depth of the longitudinal slot 30a. Therefore, negative pressure can be stored before the inner needle begins to retract by the anchoring of the stopper 28a with the stopper 32. As a result, force for sucking tissue sections may be further enhanced.

Figure 11:
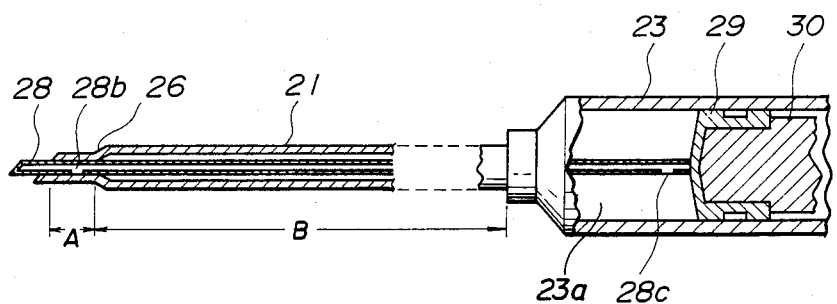
FIG. 11 is a partial sectional view for explaining an inner needle portion in the third embodiment of the present invention.

The biopsy needle set according to the third embodiment of the present invention is constructed, as shown in FIG. 11, unlike the first embodiment in such that the inner needle 28 has a tubular form the tip of which is closed, and an aperture 28b and another aperture 28c are defined in the front portion of the inner needle 28 and the rear portion of the inner needle 28, respectively. In the above construction, suction force is produced when the inner needle 28 pass through the close contact section A because negative pressure is transmitted through two passages, i.e., one of which is a gap defined between the outer needle 21 and the inner needle 28, the other of which is a passage formed by communicating the aperture 28b with the aperture 28c defined in the inner needle 28, respectively. Hence, even if tissue sections containing a comparatively large quantity of tissue liquid are sucked into the outer needle 21, decrease in suction force can be avoided, because there are provided two passages for failsafety. As a consequence, suction force can be stably maintained so that failure cases in collecting test specimens can remarkably be reduced.

As described above, according to the present invention, the biopsy needle set is constructed in such that a closely contacting part with the inner needle 28 is formed on the end of the outer needle 21 while a middle part of the outer needle 21 having a gap for communicating negative pressure is made to be as small as possible in outer diameter. In such biopsy needle described above, therefore, negative pressure produced in the cylinder 23 by withdrawing the plunger 30 is efficiently transmitted to the end of the outer needle 21 so that tissue sections can certainly be collected from a diseased part by intensive suction force with decreasing a pain in the patient.

In the claims:

1. A biopsy needle set for taking tissue specimens consisting of a cylinder, a plunger slidably located within said cylinder and a hollow outer puncturing needle secured to one end of said cylinder, an inner needle having a front and rear end and a uniform diameter along its entire length, said inner needle being slidably and axially located within said hollow outer puncturing needle and being secured at its rear end to one end of said plunger, said outer needle having a first section wherein the inside wall of said outer puncturing needle is in close contact with said inner needle at the distal end of said outer puncturing needle, and a second section extending from said first section which is not in close contact with said inner needle and comprises the portion of said outer puncturing needle which is attached to said cylinder, whereby retracting said plunger within said cylinder creates a negative pressure within the biopsy needle set thereby facilitating removal of the tissue specimen.

2. A biopsy needle set as claimed in claim 1 wherein said outer needle further has a third section, said third section extending from the second section and being attached to the cylinder, said third section further having an inner cross-section greater than that of said second section to eliminate resistance to air flow caused by movement of the inner needle therethrough.

3. A biopsy needle set as claimed in claim 1 wherein the portion of the cylinder not attached to the outer needle is provided with a notched split being symmetrical with respect to the longitudinal axis, and having a retainer for said plunger defined at the end of said notched split, a cylinder end cap fastened to said cylinder at the end removed from the puncturing needle, and a plunger knob disposed at the end of said plunger proximate said cylinder end cap adapted to be slidable in said notched split.

4. A biopsy needle set as claimed in claims 1 or 2 wherein the plunger is provided with a longitudinal slot of desired length and an inner needle retention shoulder at the open end of of said longitudinal slot, said inner needle being axially located within said longitudinal slot and being provided with stop shoulder at the rear end thereof.

5. A biopsy needle set as claimed in claim 1 or 2 wherein said inner needle is tubular in shape, has an elongated sidewall and a closed tip, an aperture defined in the front end of said sidewall and another aperture defined in the rear end of said sidewall.

6. A biopsy needle set as claimed in claim 2 wherein the portion of the cylinder not atached to the outer needle is provided with a notched split being symmetrical with respect to the longitudinal axis and having a retainer for said plunger defined at the end of said notched split, a cylinder end cap mounted on the end of said cylinder removed from the puncturing needle, and a plunger knob disposed at the end of said plunger proximate said cylinder end cap adapted to be slidable in said notched split.

7. A biopsy needle set as claimed in claims 3 or 6 wherein the plunger is provided with a longitudinal slot of desired length and an inner needle retention shoulder at the open end of said longitudinal slot, said inner needle being axially located within said longitudinal slot and being provided with a stop shoulder at the rear end thereof.

8. A biopsy needle set as claimed in claims 3 or 6 wherein said inner needle is tubular in shape, has an elongated sidewall and a closed tip, an aperature defined in the front end of said sidewall and another aperture defined in the rear end of said sidewall.

* * * * *